US00PP19829P2

(12) United States Plant Patent
Delabroye

(10) Patent No.: US PP19,829 P2
(45) Date of Patent: Mar. 17, 2009

(54) ***LEUCANTHEMUM* PLANT NAMED 'SANTE'**

(50) Latin Name: *Leucanthemum*
Varietal Denomination: Santé

(75) Inventor: Sandrine Delabroye, Hantay (FR)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 12/012,288

(22) Filed: Feb. 1, 2008

(51) Int. Cl.
*A01H 5/00* (2006.01)

(52) U.S. Cl. ..... Plt./263.1
(58) Field of Classification Search ..... Plt./263.1, Plt./285
See application file for complete search history.

*Primary Examiner*—Annette H Para
(74) *Attorney, Agent, or Firm*—Audrey Charles

(57) ABSTRACT

A new and distinct cultivar of *Leucanthemum* plant named 'Santé', characterized by its white-colored anemone-type flowers with numerous disc florets, yellow green-colored foliage, very strong stems and peduncles, and moderately vigorous, conical, and upright growth habit.

2 Drawing Sheets

Latin name of genus and species of plant claimed: *Chrysanthemum leucanthemum.*
Variety denomination: 'Santé'.

BACKGROUND OF THE INVENTION

The present invention relates to a new and distinct cultivar of *Leucanthemum* plant botanically known as *Chrysanthemum leucanthemum* and hereinafter referred to by the cultivar name 'Santé'.

The new *Leucanthemum* originated from a chance cross-pollination made by the Inventor in Hantay, France in 2004 of two unknown seedling selections of *Chrysanthemum leucanthemum.* The new *Leucanthemum* was discovered and selected by the Inventor as a single flowering plant within the progeny of the stated chance cross-pollination grown in a controlled environment in Hantay, France in 2007.

Asexual reproduction of the new cultivar by terminal stem cuttings since 2007 at Hantay, France has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Santé' as a new and distinct cultivar of *Leucanthemum* plant:

1. White-colored anemone-type flowers with numerous disc florets;
2. Yellow green-colored foliage;
3. Very strong stems and peduncles; and
4. Moderately vigorous, conical, and upright growth habit.

Of the many commercially available *Leucanthemum* cultivars, the most similar in comparison to the new cultivar is 'Sunny Side Up', U.S. Plant Pat. No. 12,837. However, in side by side comparisons, plants of the new cultivar differ from plants of 'Sunny Side Up' in the following characteristics:

1. Plants of the new cultivar have significantly more disc florets than plants of 'Sunny Side Up';
2. Plants of the new cultivar have a disc floret color different from plants of 'Sunny Side Up'; and
3. Plants of the new cultivar have an inflorescence type different from plants of 'Sunny Side Up'.

In addition, plants of the new cultivar can be compared to 'Angel', U.S. Plant Pat. No. 14,289. Plants of the new cultivar differ from plants of 'Angel' in the following characteristics:

1. Plants of the new cultivar have significantly more disc florets than plants of 'Angel'; and
2. Plants of the new cultivar have a disc floret color different from plants of 'Angel'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Santé'. The plants were field grown for approximately one year in Hillegom, The Netherlands.

The photograph on the first sheet is a side perspective view of typical plants of 'Santé' grown in an outdoor nursery.

The photograph at the top of the second sheet is a close-up view of a typical inflorescence of 'Santé'.

The photograph at the bottom of the second sheet is a close-up view of a typical leaf of 'Santé'.

DETAILED BOTANICAL DESCRIPTION

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined in July, 2007 under natural light conditions in Hillegom, The Netherlands when day temperatures ranged from 12° C. to 30° C. and night temperatures ranged from 5° C. to 16° C.

Plants used in the following description were field grown in Hillegom, The Netherlands, in an outdoor nursery and under conditions which closely approximate commercial production conditions. The plants were grown for approximately one year. Measurements and numerical values represent averages of typical plants.

Botanical classification: *Chrysanthemum leucanthemum* cultivar 'Santé'.

Parentage:

*Female parent.*—Unknown *Chrysanthemum leucanthemum.*

*Male parent.*—Unknown *Chrysanthemum leucanthemum.*

Propagation:

*Type cutting.*—Terminal stem.

*Time to produce a rooted cutting during the spring with an average air temperature of 20° C.*—Approximately 30 days.

*Root description.*—Fleshy having an average thickness of 3.0 mm.

*Rooting habit.*—Freely branching.

Plant description:

*Commercial crop time.*—Approximately 30 weeks from a rooted cutting to saleable plant.

*Growth habit and general appearance.*—Moderately vigorous, conical, and upright growth habit.

*Size.*—Height from soil level to top of plant plane: Approximately 44.7 cm. Width: Approximately 17.9 cm.

*Branching habit.*—Moderately freely branching, pinching not required, but will improve branching. Quantity of lateral branches per plant: Approximately 1.

*Lateral branch.*—Strength: Very strong. Length: Approximately 28.5 cm. Diameter: Approximately 6 mm. Length of central internode: Approximately 1.4 mm. Texture: Sparsely pubescent with hairs of approximately 0.5 mm in length. Pubescence color: 157D. Color of mature stem: 146A with shallow ribs of 143A.

Foliage description:

*General description.*—Durability to stress: High. Quantity of leaves per lateral branch: Approximately 17. Fragrance: None. Form: Simple. Arrangement: Alternate.

*Leaves.*—Aspect: Acute angle to stem, sessile. Shape: Lanceolate to elliptic. *Margin.*: Dentate with an average of 3 teeth per cm teeth, which have an average length of 2.5 mm. Apex: Acute. Base: Cuneate, short decurrent. Venation pattern: Pinnate. Length of mature leaf: Approximately 9.9 cm. Width of mature leaf: 2.5 cm. Texture of upper surface: Glabrous, moderately glossy. Texture of lower surface: Sparsely pubescent along midvein with hairs of approximately 0.4 mm in length. Pubescence color: 157D. Color of upper surface of young and mature foliage: 137A with venation of between 144A and 144B. Color of lower surface of young and mature foliage: 146B with venation of between 146B and 146C.

Flowering description:

*Flowering habit.*—'Santé' is a perennial plant freely flowering under outdoor growing conditions with substantially continuous blooming from summer to late summer.

*Lastingness of individual inflorescence on the plant.*—Approximately 3 weeks.

Inflorescence description:

*General description.*—Type: Anemone, solitary capitula, self-cleaning. Inflorescences open in order of development. Florets open acropetally. Aspect: Upright. Shape: Round. Arrangement: Terminal and axillary capitula. Disc and ray florets arranged with numerous central disc florets and two rows of ray florets on a receptacle having three rows of involucral bracts. Quantity of inflorescences per lateral stem: Approximately 5. Diameter: Approximately 6.8 cm. Depth: Approximately 3.2 mm. Fragrance: None:

*Peduncle.*—Strength: Very strong. Aspect: Terminal is erect, others at acute angle to stem. Length of terminal peduncle: Approximately 1.8 cm. Length of fourth peduncle: Approximately 15.8 cm. Length of seventh peduncle: Approximately 23.5 cm. Diameter of all peduncles: Approximately 4.0 mm. Texture: Glabrous, slightly glossy with shallow axial ribs. Color: 146A with axial ribs of 143A.

*Bud.*—Rate of opening: Generally takes approximately one week for bud to progress from first color to fully open flower. Quantity of buds per lateral stem: Approximately 3.

*Bud just before opening.*—Shape: Flattened globular. Length: 9 mm. Diameter: Approximately 1.2 cm. Color: Between 137D and 138A.

*Ray florets.*—Quantity per inflorescence: Approximately 29. Arrangement: Rotate in a two whorls. Aspect: Slightly downward turning having an average angle of 45°. Shape: Narrow oblong. Margin: Entire. Apex: Retuse. Base: Attenuate. Length: Approximately 2.9 cm. Width: Approximately 9.0 mm. Texture of upper and lower surfaces: Glabrous. Color of upper and lower surfaces when first open: 157D with 145C at base. Color of upper and lower surfaces when fully open: 155C with between 145C and 145D at base.

*Disc florets.*—Quantity per inflorescence: Approximately 500. Arrangement: Spirally arranged on disc in center of inflorescence. Shape: Rotate. Margin: Entire. Apex: Acute. Base: Lower third fused into a tube. Length: Approximately 1.7 cm. Diameter at apex: Approximately 1.4 cm. Diameter at base: Approximately 1.0 mm. Texture: Glabrous. Color when first open: 151C with between 145B and 145C at base. Color when fully open: Between 145C and 145D at base transitioning to a midsection and apex of 155C.

*Disc.*—Diameter: Approximately 1.5 cm.

*Receptacle.*—Shape: Broad conical. Height: Approximately 5.0 mm. Diameter: Approximately 2.7 cm.

*Phyllaries.*—Quantity per inflorescence Approximately 45. Arrangement: In three whorls. Shape: Ovate. Margin: Entire. Apex: Broadly acute. Base: Broadly cuneate. Length: Approximately 6.0 mm. Width: Approximately 3.0 mm. Texture of upper and lower surfaces: Glabrous, slightly glossy. Color of upper surface: 144A with margins of N199C. Color of lower surface: Between 137B and 137C with margins of N199C.

*Reproductive organs.*—Androecium: Present on disc florets only. Stamen quantity: 5 per floret. Stamen length: Approximately 1.8 mm. Anther shape: Linear, basifixed. Anther length: Approximately 1.0 mm. Anther color: Between 164B and 164C. Pollen amount: Sparse. Pollen color: 22A. Gynoecium: Present on ray and disc florets. Pistil quantity: 1 per floret. Pistil length: Approximately 5.0 mm. Stigma shape: Decurrent. Stigma color: between 153C and 153D. Style length: Approximately 4.0 mm. Style color: 145D. Ovary color: 145D.

Seed and fruit production: Neither seed nor fruit production has been observed.

Disease and pest resistance: Resistance to pathogens and pests common to *Leucanthemum* has not been observed.

Weather tolerance: Plants of the new *Leucanthemum* have been observed to be hardy to USDA zone 6 and tolerate high temperatures to at least 40° C., and to demonstrate moderate tolerance to rain effects and high tolerance to wind effects.

What is claimed is:

1. A new and distinct cultivar of *Leucanthemum* plant named 'Santé', substantially as herein shown and described.

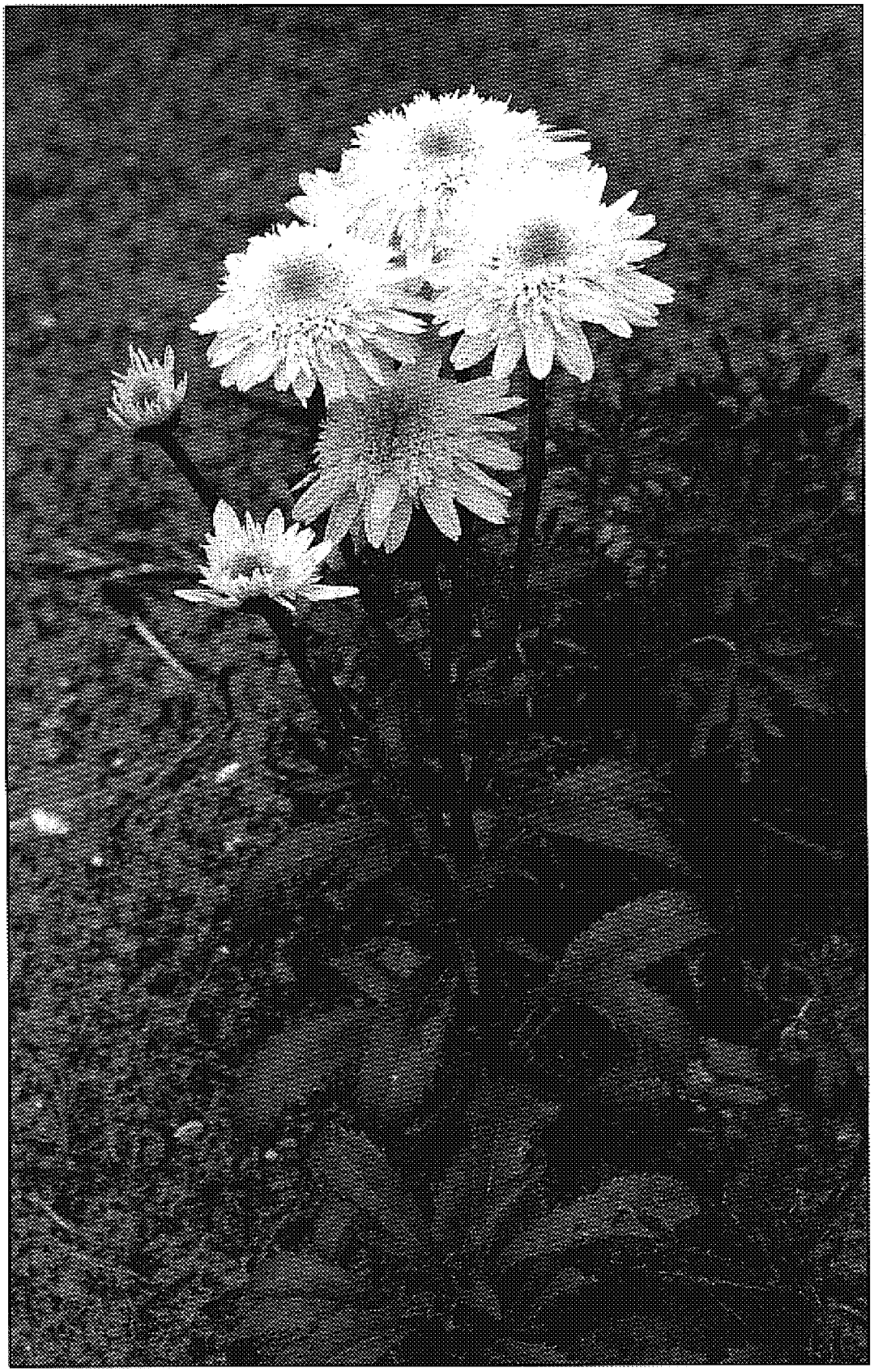

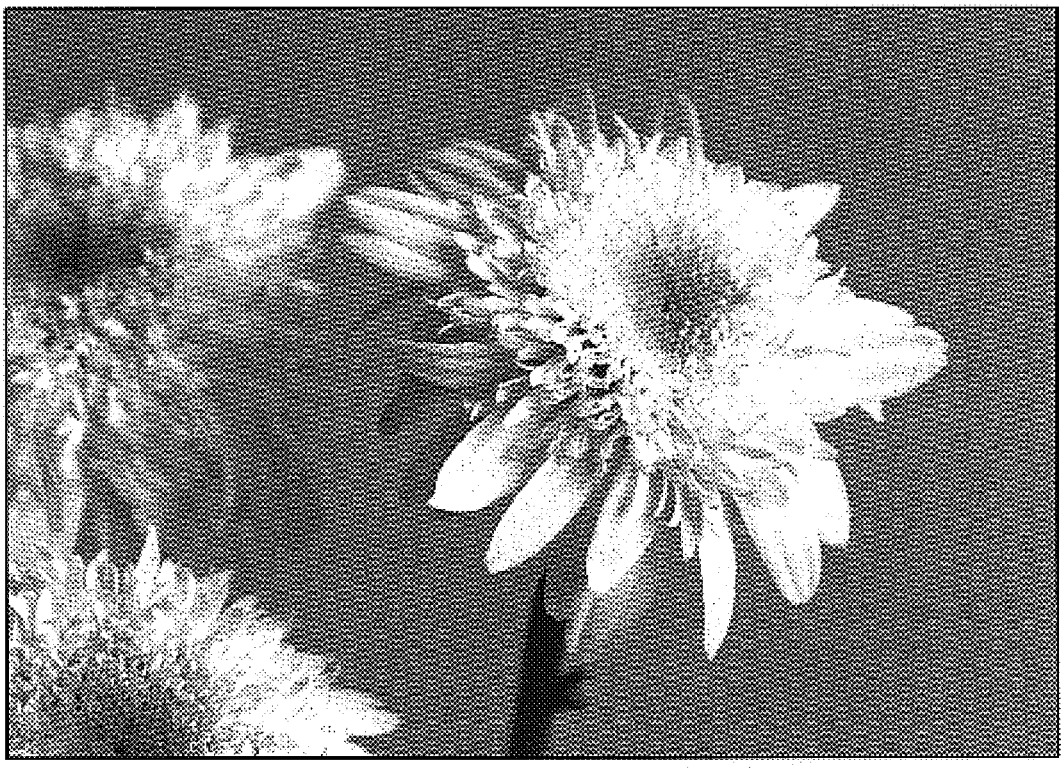
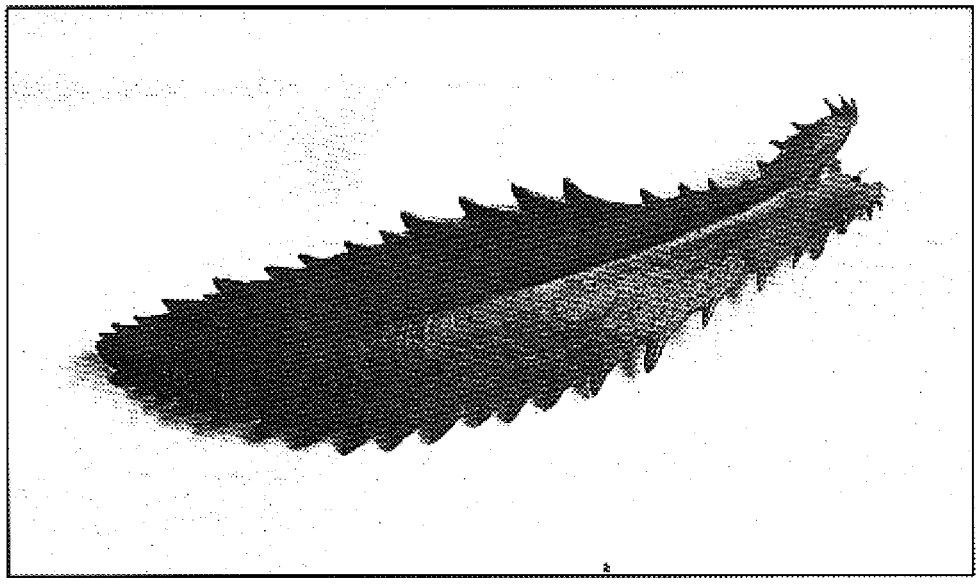

* * * * *